(12) United States Patent
Friedel et al.

(10) Patent No.: US 6,823,727 B2
(45) Date of Patent: Nov. 30, 2004

(54) DEVICE HAVING A SENSOR ARRANGEMENT FOR DETERMINING THE AMBIENT-AIR QUALITY AND AN ARRANGEMENT OF OZONE SENSORS UPSTREAM AND DOWNSTREAM OF A RADIATOR WHICH IS COATED WITH A CATALYST MATERIAL, AND METHOD FOR OPERATING A DEVICE OF THIS TYPE

(75) Inventors: Joerg Friedel, Wenzenbach/Gruenthal (DE); Hans-Peter Göttler, Regensburg (DE); Anton Grabmaier, Zeitlarn (DE)

(73) Assignee: Siemens Aktiengesellschaft, München (DE)

( * ) Notice: Subject to any disclaimer, the term of this patent is extended or adjusted under 35 U.S.C. 154(b) by 70 days.

(21) Appl. No.: 10/229,663

(22) Filed: Aug. 27, 2002

(65) Prior Publication Data

US 2003/0066335 A1 Apr. 10, 2003

(30) Foreign Application Priority Data

Aug. 31, 2001 (DE) .......................... 101 42 711

(51) Int. Cl.[7] .......................... G01M 19/00; G01N 7/00
(52) U.S. Cl. .................... 73/118.1; 73/31.01; 73/31.02
(58) Field of Search ...................... 73/118.1, 31.01, 73/31.02, 31.03; 701/29

(56) References Cited

U.S. PATENT DOCUMENTS

| 4,482,007 A | * | 11/1984 | Yoshimi et al. ............. 165/225 |
| 4,733,605 A | * | 3/1988 | Holter et al. ................. 454/75 |
| 5,320,577 A | * | 6/1994 | Tooru et al. .................. 454/75 |
| 5,755,380 A | * | 5/1998 | Virey ..................... 237/12.3 R |
| 5,811,662 A | * | 9/1998 | Williams et al. ........... 73/31.06 |
| 6,026,639 A | * | 2/2000 | Kumar ......................... 60/274 |
| 6,170,318 B1 | * | 1/2001 | Lewis ....................... 73/23.34 |
| 6,214,303 B1 | * | 4/2001 | Hoke et al. ................. 423/210 |
| 6,340,066 B1 | * | 1/2002 | Dettling et al. ............ 180/54.1 |
| 6,503,462 B1 | * | 1/2003 | Michalakos et al. ........ 422/173 |
| 6,681,619 B2 | * | 1/2004 | Alleving et al. ........... 73/118.1 |
| 2002/0000088 A1 | * | 1/2002 | Alleving et al. .............. 60/277 |
| 2004/0020359 A1 | * | 2/2004 | Koermer et al. ............. 95/113 |

FOREIGN PATENT DOCUMENTS

| DE | 4007965 | 9/1991 |
| DE | 4213778 | 5/1993 |
| DE | 0789200 | 8/1997 |
| DE | 69224105 | 5/1998 |
| DE | 19700964 | 7/1998 |
| DE | 69511385 | 12/1999 |
| EP | 0431-648 A1 | * 6/1991 |
| EP | 0431648 | 6/1991 |
| EP | 1125588 | 8/2001 |

* cited by examiner

Primary Examiner—Michael Cygan
(74) Attorney, Agent, or Firm—Martin A. Farber

(57) ABSTRACT

Device, in particular for use in a motor vehicle, having a sensor arrangement (21), which controls an air-conditioning unit, for determining the ambient-air quality, and an arrangement of ozone sensors (21, 22) upstream and downstream of a radiator (1), in particular of the motor vehicle, which is coated with a catalyst material for detecting the conversion rate of the conversion of ozone into oxygen which is effected by the catalyst.

6 Claims, 3 Drawing Sheets

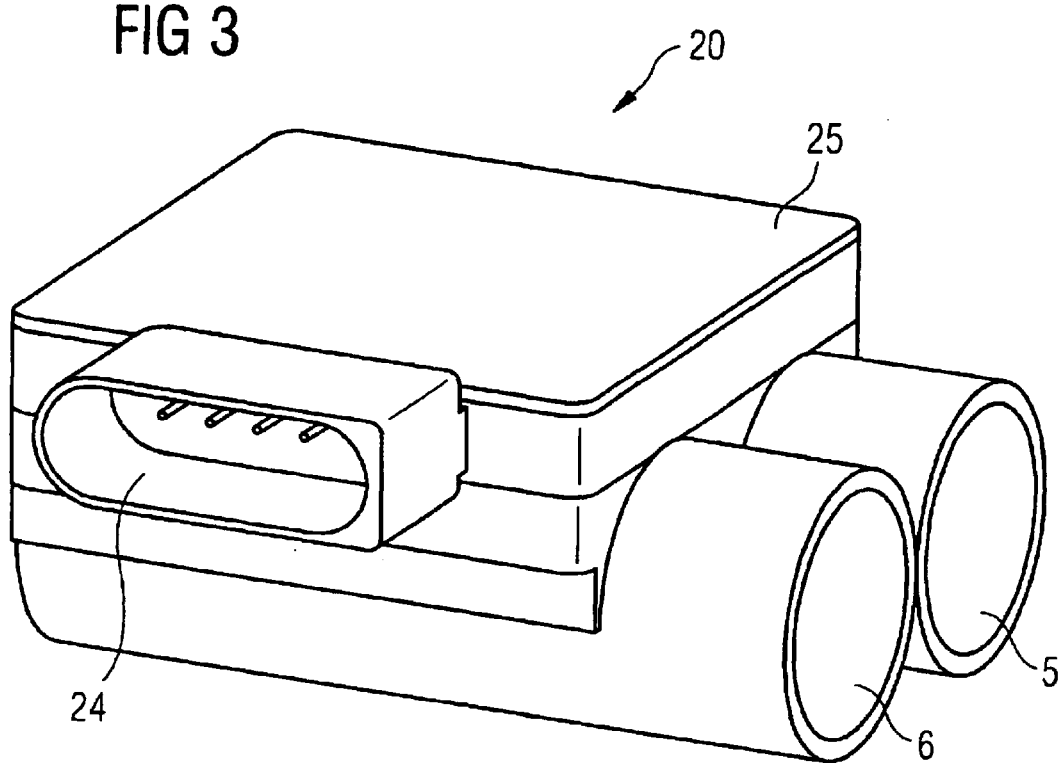

DEVICE HAVING A SENSOR ARRANGEMENT FOR DETERMINING THE AMBIENT-AIR QUALITY AND AN ARRANGEMENT OF OZONE SENSORS UPSTREAM AND DOWNSTREAM OF A RADIATOR WHICH IS COATED WITH A CATALYST MATERIAL, AND METHOD FOR OPERATING A DEVICE OF THIS TYPE

FIELD AND BACKGROUND OF THE INVENTION

Device having a sensor arrangement for determining the ambient-air quality and an arrangement of ozone sensors upstream and downstream of a radiator which is coated with a catalyst material, and method for operating a device of this type For reasons of environmental and personal protection, the levels of pollutants which result from motor vehicles with an internal combustion engine or from the generation of energy using stationary combustion installations have to be reduced considerably.

A new approach aimed at reducing the levels of pollutants consists in actively removing pollutants not directly from the exhaust-gas stream from a combustion installation, but rather from the ambient air. This route is promising in particular for the removal of ground-level ozone, which has a considerable influence on how people feel on account of its strongly oxidizing action. Ozone itself is not a gas which is emitted directly and therefore cannot be removed in the exhaust-gas stream. It is formed when nitrogen oxides are present in outside air under solar radiation, on account of the UV component of this radiation, as a result of complex photochemical reaction equilibria.

Since ozone is extremely reactive, it can easily be broken down quantitatively by means of a catalyst system through which air flows. These catalysts are extremely stable, since there is no need for any direct action of strong oxidation catalysts, which are highly sensitive to poisoning, such as for example platinum. Systems which substantially effect adsorption of the ozone on a surface are sufficient; this ozone then breaks down instantaneously to form oxygen.

Catalyst systems of this type have long been in use in passenger aircraft which fly close to the ozone layer, where they are used to treat the air which is passed into the passenger compartment. Recently, such systems have also been deployed in motor vehicles. Here, the radiator of the vehicle is coated with the catalyst. The large quantities of air flowing through the radiator are quantitatively cleaned of ozone, i.e. the vehicle cleans the ambient air.

A system of this type represents a component of relevance in terms of the exhaust gas. The legislators in increasing numbers of countries are imposing an on-board diagnosis system for all components which are relevant to the exhaust gas. Therefore, a suitable sensor system is also required for an ozone-cleaning system.

Particularly in densely populated areas, local pollutant peaks occur and have an adverse effect at least on the feeling of wellbeing if not even on the health of people. Such high pollutant concentrations may occur, for example, in underpasses or tunnels. Traffic queues may also be considered critical in this respect.

Conventional vehicle ventilation systems supply highly polluted ambient air to the interior of the vehicle and therefore to the driver of the vehicle. However, it is already known from the prior art to use suitable sensors to detect an extremely high level of pollutants in the ambient air. As a function of this, the supply of air to the interior of the vehicle is regulated or interrupted from time to time. Sensors of this type are sensitive in particular to gases such as NOx, CO and HC.

A control operation of this type may be initiated as a result of the vehicle driving into a busy road tunnel or as a result of a vehicle stopping behind a truck at traffic lights. Therefore, a very rapid response of the sensor arrangement is particularly necessary.

SUMMARY OF THE INVENTION

The object of the invention is to provide an improved ambient-air quality sensor arrangement and diagnosis in particular in a motor vehicle.

According to the invention, the device according to the invention, in particular for use in a motor vehicle, is designed with a sensor arrangement, which controls an air-conditioning unit, for determining the ambient-air quality and an arrangement of ozone sensors upstream and downstream of a radiator, in particular of the motor vehicle, which is coated with a catalyst material for detecting the conversion rate of the conversion of ozone into oxygen which is effected by the catalyst.

Therefore, the invention proposes a sensor arrangement which combines both the task of ambient-air quality measurement and the task of functional diagnosis for an ozone converter with one another and therefore makes it possible to utilize synergy effects which result. The use of sensors of similar types for both applications, namely ambient-air quality measurement and ozone conversion functional diagnosis, and the resulting substantially identical demands imposed on the control and evaluation electronics, lead to space and cost savings.

In an advantageous refinement of the invention, the sensor arrangement for determining the air quality and the ozone sensor for determining the ozone level upstream of the radiator are arranged in a common first airstream. This on the one hand saves space and on the other hand ensures that all the values determined originate from the same location. Therefore, it is on the one hand advantageously possible for the ozone level to be included in the determination of the air quality and on the other hand for the measured values for the air quality to be used to correct the measured ozone level, since the ozone sensors have a cross-sensitivity with respect to other gases, and therefore the ozone measured value is subject to certain error boundaries.

In a particularly advantageous refinement of the invention, both the first airstream and a second airstream, in which the ozone concentration downstream of the radiator is measured, are accommodated in a common housing, in which, in a particularly advantageous configuration of the device according to the invention, a control unit which processes the signals from the sensors is also arranged. This advantageously allows the signals from all the sensors to be processed from just one, centrally arranged control unit. In a development of the invention, this control unit can also be used to control heating elements arranged at the sensors.

In an advantageous refinement of the invention, all the signals and supply voltages can be passed via a single plug connector and therefore via only a single cable, which considerably simplifies installation in particular in a motor vehicle.

In principle, it is also possible for a dedicated airstream passage with a specific sensor arranged therein to be provided for each gas which is to be detected. It is essential for the invention for all the passages to run in one housing. In addition to ozone, examples of gases which are to be detected may be CO, NOx or HC.

BRIEF DESCRIPTION OF THE DRAWINGS

The invention is explained in more detail below with reference to an exemplary embodiment and with the aid of figures, in which:

FIG. 3 shows the assembled housing from FIG. 2.

DETAILED DESCRIPTION OF THE PREFERRED EMBODIMENTS

Figure 1:
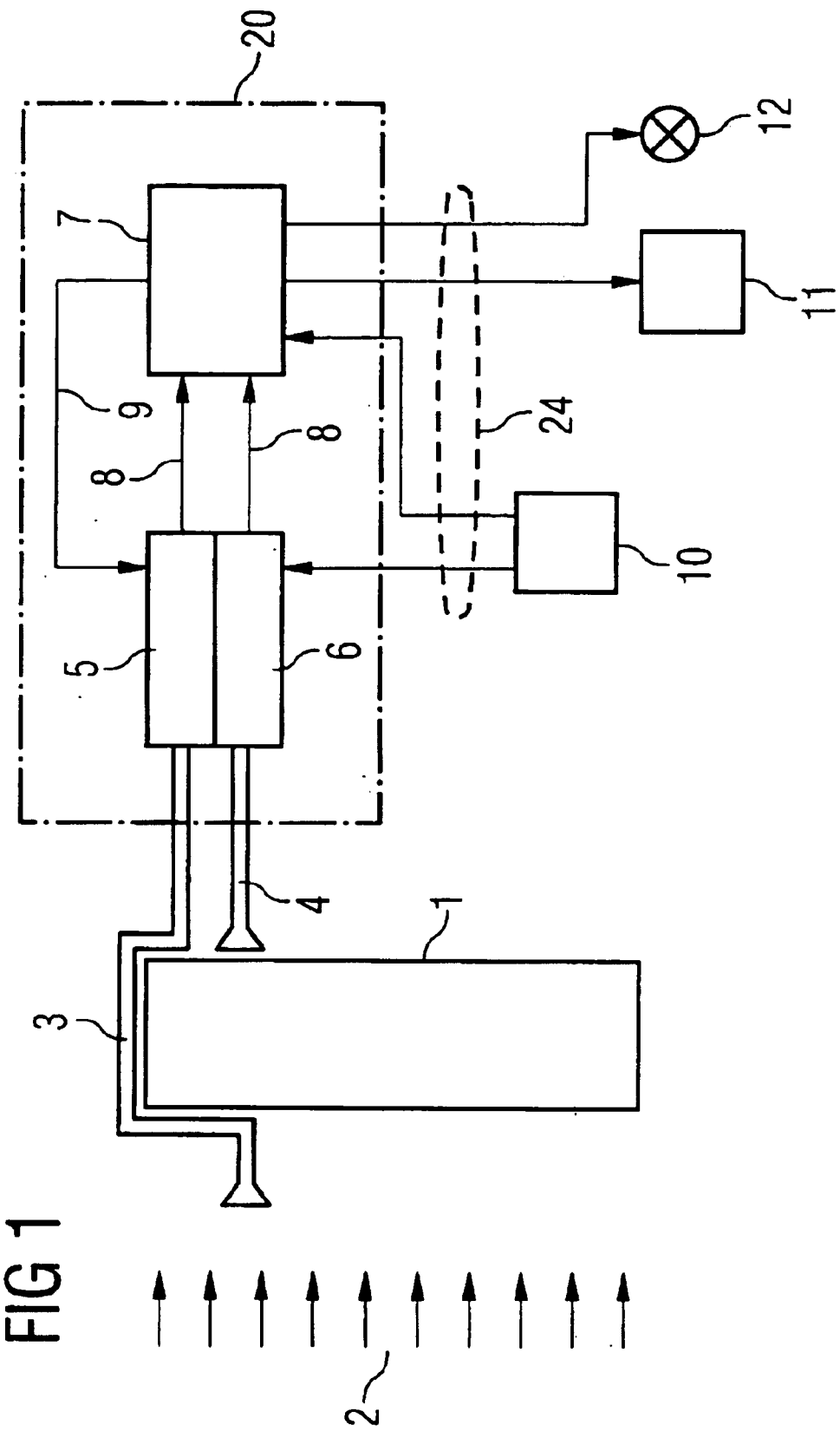
FIG. 1 shows an outline illustration of a device according to the invention.

In the illustration shown in FIG. 1, an ambient-airstream 2 flows to a radiator 1. The radiator 1 is coated with a catalyst for breaking down ozone. The end of a first air-receiving pipe 3 is arranged upstream of the radiator 1, and the end of a second air-receiving pipe 4 is arranged downstream of the radiator 1. The air-receiving pipes 3, 4 are connected to a housing 20 of a device according to the invention for determining the ambient-air quality and for detecting the conversion rate at which ozone is converted into oxygen.

Figure 2:
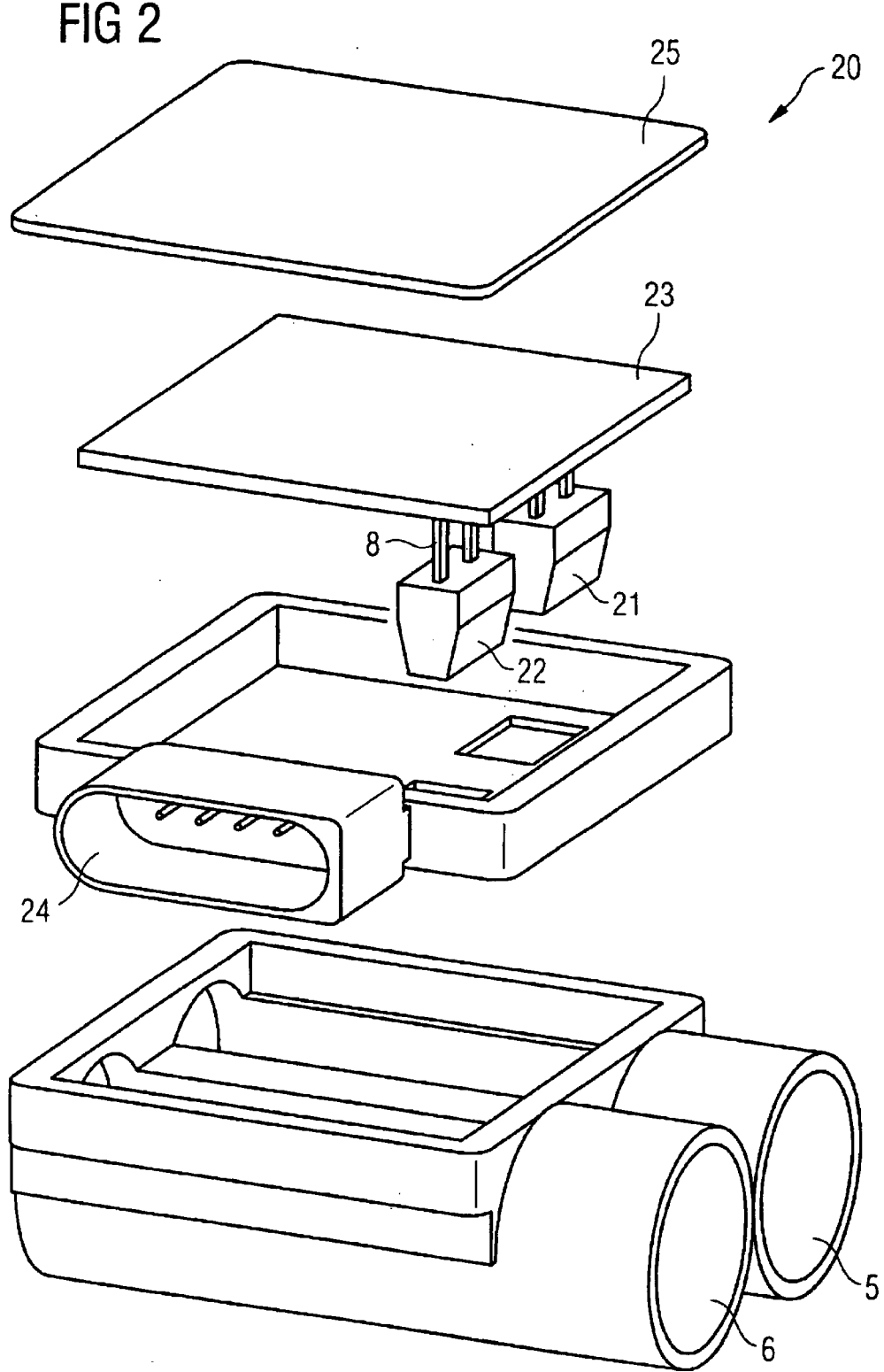
FIG. 2 shows an exploded view of an exemplary embodiment of a housing of a device according to the invention.

As can be seen in more detail from FIGS. 2 and 3, the housing 20 has two passages 5 and 6 for receiving the airstreams supplied through the air-receiving pipes 3, 4. Gas sensors or gas sensor arrays 21 and 22 which are each sensitive to different gases are arranged in the passages 5 and 6.

Sensors 21 for ozone ($O_3$) and at least carbon monoxide (CO) are preferably arranged in the first passage 5. Furthermore, it is advantageous to provide further sensors for nitrogen oxides (NOx) and hydrocarbons (HC), and it is possible for further sensors to be provided depending on the specific application.

Essentially a second ozone sensor 22 is arranged in the second passage 6, in order to detect the ozone concentration downstream of the radiator 1 which is provided with a catalyst for ozone conversion, so that it can be determined that the ozone conversion is functioning correctly from the ratio of the measured value from the first ozone sensor in the first passage 5 and the measured value from the second ozone sensor in the second passage 6. However, it is also possible for further sensors to be arranged in the second passage 6.

The sensors are connected to a printed-circuit board 23, on which in particular a control unit 7 which processes the measured values from the sensors 21, 22 is arranged. The control unit 7 is preferably designed as a microprocessor. It is connected to the sensors 21, 22 via lines 8.

The control unit 7 uses the values supplied by the sensors 21, 22 to determine on the one hand a value for the air quality, and controls an air-conditioning unit 11 accordingly. In this unit, for example above a predetermined threshold value for the air quality, the recirculated air flap in a vehicle is closed. The device which is designed in accordance with the invention and in which all the values are determined in one housing and are processed by one control unit, makes it possible for the measured values to be combined in different variants in order for them to be adapted to corresponding requirements.

Moreover, the control unit 7 controls a display device 12 which, when used in a motor vehicle, indicates to the driver whether the ozone conversion is functioning correctly. By way of example, a warning light may illuminate if a conversion rate falls below a predetermined level. It is also conceivable for the current conversion rate to be displayed continuously.

The sensors 21 and 22 and the control unit 7, as well as any further circuit parts, are supplied with supply voltages by a voltage-supply unit 10. All the voltages or signals which are passed to the outside or come from the outside are passed via just one plug connector 24, allowing very simple installation in particular for use in a motor vehicle.

Both the abovementioned application areas of the sensors 21 and 22, namely the determination of the air quality and the determination of the ozone conversion rate, are predestined for the use of thin-film gas sensors based on metal oxide. Sensors of this type are technologically advanced and have long proven their worth in a wide range of technical applications. The application areas include the monitoring of combustion installations, the detection of leaks, air-quality monitoring systems and, to an increasing extent, applications in the automotive sector.

Thin-film gas sensors based on metal oxide have preferred gas reactions on account of specific surface, temperature, volume and geometry variations and, on account of their thermodynamic stability in the active layers, are widely accepted. Production by means of simple standard processes allows inexpensive mass production with a high level of process stability. A further advantage is the possibility of influencing the sensor properties by varying the contact geometry and by selecting suitable dopants and catalysts.

Normally, suitable electrode structures are provided both for the active heating of the sensor elements and for the measurement of the sensor resistances. Both a single-sided structure and a two-sided structure are conceivable. The heating is generally designed as a simple heating coil, while various interdigitated structures are used as measurement electrodes.

The abovementioned semiconductor gas sensors require operating temperatures of several hundred degrees. Their resistance changes according to the concentration of target gas. The heating structures integrated in the sensors 21, 22 can be controlled by means of suitable electronics in the form of the control unit 7. The sensor heaters are actuated via a line 9, preferably by means of pulse-width modulation. The heater resistance and therefore the heater or sensor temperature can be determined by means of a measurement shunt. An additional constant heating voltage can prevent the sensors from cooling too quickly between the heating phases. As soon as the appropriate operating temperature is reached, the corresponding sensor resistance can be measured, and this in turn represents a measure of the concentration of a target gas.

The use of common electronics, preferably microprocessor-based, also allows the ozone concentration in the ambient air to be used as a further criterion in the assessment of the air quality. A standard limit level for the maximum ozone concentration is 180 $\mu g/m^3$.

It is currently almost impossible to achieve a 100% selectivity of a semiconductor gas sensor. There are always certain residual cross-sensitivities which have an adverse effect on the sensor accuracy. A high sensor reliability and low sensor tolerance is required in particular for the determination of the ozone conversion rate. Since the standard concentration of ozone in air is up to three orders of magnitude (factor of 1000) lower than the other smog gases, it is particularly important to compensate for the cross-sensitivities in this context.

The use of the multiselective gas sensor array according to the invention makes it possible to establish the presence of relevant gases with a cross-sensitivity for the ozone sensor arrangement and even for the presence of these gases to be recorded quantitatively. Therefore, it is in turn possible to carry out any correction to the ozone measured values which may be required.

As shown in FIGS. 2 and 3, the device according to the invention can be accommodated in a simple and therefore inexpensive way in a single housing 20. As a result, the device can be used as a mass-produced product in motor vechicles.

The embodiment of the housing 20 which is illustrated in FIGS. 2 and 3 has only the passages 5 and 6 for carrying air, a plug connector 24, a printed-circuit board 23 with gas senors 21, 22 which are arranged thereon and project into the air passages 5 and 6, and a cover 25 which closes off the housing 20. The housing 20 is therefore of simple structure and is easy to fit.

What is claimed is:

1. Device, in particular for use in a motor vehicle, having a sensor arrangement (21), which controls an air-conditioning unit, for determining ambient-air quality, and an arrangement of ozone sensors (21, 22) upstream and downstream of a radiator (1), in particular of the motor vehicle, which is coated with a catalyst material for detecting conversion rate of conversion of ozone into oxygen which is brought about by the catalyst;

wherein both the sensors (21) of the sensor arrangement and ozone sensors (22) are connected to a common control unit (7), which processes the signals from the sensors;

a first airstream (3, 5) and a second airstream (4, 6), in which the ozone sensor (22) for determining the ozone level downstream of the radiator (1) is arranged, are guided in passages (5, 6) which are arranged in a common housing, (20), wherein the control unit (7) is also arranged in the common housing (20); and the housing (20) has only one plug connection (24), via which all required voltages and signals are passed.

2. Device according to claim 1, wherein the sensor arrangement (21) for determining the air quality and the ozone sensor for determining ozone level upstream of the radiator (1) are arranged in a common first airstream (3, 5).

3. Device according to claim 2, wherein the first airstream (3, 5) and a second airstream (4, 6), in which the ozone sensor (22) for determining the ozone level downstream of the radiator (1) is arranged, are guided in passages (5, 6) which are arranged in a common housing (20).

4. Device according to claim 1, wherein the sensors (21, 22) have heating elements which are controllable by the control unit (7).

5. A method for use in a device according to claim 1, wherein measured values from the ambient-air quality sensor arrangement (21) are used to compensate for measurement inaccuracies of the ozone sensors (22) resulting from cross-sensitivities of the ozone sensors (22).

6. The method for use in a device according to claim 5, wherein the measured value from the ozone sensor arranged upstream of the radiator (1) is also taken into account for determination of the ambient-air quality.

* * * * *